(12) United States Patent
Vitello (10) Patent No.: US 8,864,021 B1
(45) Date of Patent: Oct. 21, 2014

(54) SUPPORT AND CLOSURE ASSEMBLY FOR DISCHARGE PORT OF A SYRINGE AND TRACKING SYSTEM THEREFORE

(71) Applicant: Jonathan J. Vitello, Fort Lauderdale, FL (US)

(72) Inventor: Jonathan J. Vitello, Fort Lauderdale, FL (US)

(73) Assignee: Medical Device Engineering, LLC., Pompano Beach, FL (US)

( * ) Notice: Subject to any disclaimer, the term of this patent is extended or adjusted under 35 U.S.C. 154(b) by 0 days.

(21) Appl. No.: 14/013,770

(22) Filed: Aug. 29, 2013

Related U.S. Application Data

(60) Provisional application No. 61/695,835, filed on Aug. 31, 2012.

(51) Int. Cl.
*G06F 17/00* (2006.01)
*A61M 5/50* (2006.01)

(52) U.S. Cl.
CPC .................................. *A61M 5/5086* (2013.01)
USPC .......................................... 235/375; 604/111

(58) Field of Classification Search
USPC .................... 235/375, 487; 604/92, 518, 111
See application file for complete search history.

(56) References Cited

U.S. PATENT DOCUMENTS

2012/0064515 A2 * 3/2012 Knapp et al. ................... 435/6.1

* cited by examiner

*Primary Examiner* — Edwyn Labaze
(74) *Attorney, Agent, or Firm* — Malloy & Malloy, P.L.

(57) ABSTRACT

A system for tracking a multi-component, tamper evident closure assembly for a pre-filled syringe along a distribution route, including a predetermined code applied to each of a plurality of components of the same closure assembly and comprising electronically readable coded indicia, is structured to identify and distinguish each of a plurality of closure assemblies from one another. A reading and recording of predetermined code for each closure assembly along the distribution route is accomplished. The location at which tampering of a closure assembly has occurred along the corresponding distribution route can be accomplished by reading the coded indicia segments on any of detached or assembled ones of the plurality of originally assembled components of the same closure assembly.

1 Claim, 5 Drawing Sheets

SUPPORT AND CLOSURE ASSEMBLY FOR DISCHARGE PORT OF A SYRINGE AND TRACKING SYSTEM THEREFORE

CLAIM OF PRIORITY

The present application is based on and a claim of priority is made under 35 U.S.C. Section 119(e) to a provisional patent application in the U.S. Patent and Trademark Office, namely, that having Ser. No. 61/695,835 and a filing date of Aug. 31, 2012, and which is incorporated herein by reference.

BACKGROUND OF THE INVENTION

1. Field of the Invention

This invention is directed to a closure assembly for the discharge port of a syringe, which may include a tamper evident structure. A supporting container or other support base is cooperatively structured with the closure to removably but fixedly support it in an operative orientation, which facilitates the rotational attachment of the syringe to the closure while still in the container. As result, the need to touch or handle the closure, in order to connect it to the syringe, is eliminated or significantly reduced. The present invention is further directed to a tracking system associated with the closure assembly. The inventive tracking system comprises visually and/or electronically readable identifying codes disposed on both the interior and exterior components of the closure assembly, and the tracking thereof along a distribution route. The distribution route may extend from initially, a point of manufacture and assembly of the closure assembly, to finally, a point of use of the pre-filled syringe on a patient, wherein the identifying codes on the closure assembly may be monitored at any of a plurality of distribution and or transport points of the closure assembly therebetween.

2. Description of the Related Art

It is very common for medical doctors and other authorized medical personnel to order that a patient be given a drug or medication by injection. In fact, it is currently estimated that more than 16 billion injections are administered on a worldwide basis in any given year. Clearly, a number of safety issues are associated with giving injections. One top concern relates to the avoidance of contamination by bacteria, germs or other microbial organisms. Because of this, and because of the potential for theft of and/or tampering with medicines intended for injection, an important concern relates to minimizing the number of people handling syringes which are filled or to be filled with medication.

As a result, it is becoming relatively common in hospital settings for a number of syringes to be pre-loaded or filled by a pharmacist, or other authorized personnel within a hospital or similar facility, at an appropriate location for subsequent dispensing of same to one or more nursing stations, and then to patients. The pharmacy or other location where syringes are filled can and often will be located in a remote part of the hospital, relative to the patient care area where the injection is to be administered. In some cases, the loading of syringes occurs in another building or facility entirely, often referred to as "third party pharmacies." This may even be a growing trend among hospitals to limit certain costs. Regardless, a syringe filling station at a large medical facility may resemble a factory, from which drug loaded syringes are delivered to a large number of nurse's stations in multiple hospital or medical buildings. Because many nurse's stations are typically located very remote and from a syringe filling station, a loaded syringe is quite often given to another person for delivery to a nurse's station, for subsequent dosing of the patient by qualified personnel.

From the foregoing, it may be understood that during the course of loading a syringe with a drug, and also afterwards, when a loaded syringe is delivered to a nurse's station, or even subsequently to a patient, the syringe can easily be handled by more than just one or two people. This, in turn, increases the chance for the syringe to become contaminated, by exposure to bacteria, germs, etc., which could possibly then be introduced into a patient's body tissues, and which could potentially lead to infection, presenting in turn, dangerous and possibly fatal effects on the patient. Consequently, and from the above, the concern for and the high level of importance associated with maintaining the sterility of a syringe will be better understood.

Also, and especially in the case of a very expensive drug or an addictive drug, such as but not limited to morphine, there is some danger that a pre-loaded syringe will be tampered with by a person seeking to improperly gain access to the drug, whether to use it himself, or to try to sell it illegally. A resulting danger also exists in that if an unauthorized person were actually to access to the prescribed medicine, he or she might inappropriately substitute saline solution or some other unauthorized substance in the syringe. By way of example only, if saline solution were substituted for a dose of morphine, this could have extremely serious consequences. Thus, the growing use of syringes which are pre-loaded with a drug presents another problem in that it is important to know if the sealed and/or pre-loaded syringe has, or has not, been tampered with and exposed to contamination or might otherwise have been compromised.

The benefits of using a pre-filled syringe, and of being able to readily determine whether or not it has been tampered with, are abundantly clear. Drugs and medications are specific to each particular patient's disorder or disease being treated. In addition, interactions between drugs and medications given to a patient incorrectly can have serious and deadly consequences. It is, therefore, important to know that a particular medication being injected is, in fact, the drug that was prescribed by the treating physician, and that it has not been replaced by another compound. Moreover, some drugs can have harmful effects in large doses. Accordingly, it is also important to ensure that the proper dosage is followed, as prescribed. Since pre-filled syringes are prepared in advance of being delivered and used, they may be loaded carefully by a pharmacist or other similarly qualified individual to ensure the appropriate medication and dose is prepared. This reduces errors on injection by nurses or physicians who may be in a stressful or time-sensitive situation and may not have the luxury of verifying the correct medication or measuring out a dose, particularly small doses, from a source vial.

Pre-filled syringes are also particularly useful in view of the recent shortage of medications and other injectables, such as narcotics or epinephrine for example. Some drugs and medications, even those which are essential for treating life-threatening diseases, are currently in drastically short supply, due to several factors. For example, during the manufacturing process of some medications, it can occur and has happened for whole batches to become contaminated, such as by bacteria or other microorganisms that could cause infection upon injection, thereby rendering quantities of medications unusable, which in turn, reduces the overall stock of available medications. In addition, manufacturing capacity issues, such the availability and increased cost of raw materials and transportation, as well as lower profit margins, are contributing factors that also result in reduced quantities of medications being produced, and therefore, available to patients. Accordingly, the supply of drugs that are available and safe for use is starting to be viewed as a precious commodity, with little to no room for waste. The use of pre-filled syringes helps significantly to ensure that only the exact amount of medicine or drugs prescribed are being used, thereby helping to eliminate waste. Also, by having a pharmacist or other qualified person at a filling station preparing the pre-filled syringes, even at a location distant from the patient treatment site helps to ensure that the exact amount of medication needed is delivered. This also circumvents the theft of drugs by "accidental" taking of excess medication, such as to siphon some off for personal use or another non-prescribed purpose, which has unfortunately been known to occur. Accordingly, the use of pre-filled syringes helps maintain the stock of these important drugs so that they may be available to the patients truly in need of them. Further, any unused pre-filled syringes may be recycled so that unused medication does not go to waste. This is only possible, however, if there is some way to determine that a pre-filled syringe has not been tampered with or compromised, thereby verifying the integrity of the contents.

Despite attempts in the past to prevent unauthorized access to syringe(s) pre-loaded with a drug or medication, it is understood that some problems continue to exist in this field of art. Such problems include the ability to manufacture syringes, and/or accessories therefor, in an inexpensive and yet effective manner. Other problems exist relative to the number of people that might handle pre-filled syringes, which in turn, poses a challenge to maintaining the sterility of the syringes and/or accessories, whether during storage at the manufacturing facility, during the transport thereof from such a facility to a hospital or other medical facility, and then to a nursing station and ultimately, to a patient care area.

Accordingly, there is a need in the relevant field of art for an improved syringe closure, which may include a tamper evident assembly that is capable of being used with standard or conventional pre-loaded syringes. If any such improved syringe closure were developed, it would be structured in a manner which overcomes problems and or disadvantages of the type set forth above or otherwise known to still exist in this field of art. In addition, the use and application of any such improved syringe closure, were one developed, would preferably be facilitated by the provision of a closure support, which may be in the form of a container or tray. Ideally, if any such combination of a closure and a support therefor were developed it would have certain structural and operative features which would facilitate appropriate connection of the closure to a conventional pre-loaded syringe in an efficient manner which would eliminate or at least significantly reduce the need for an individual to directly handle or touch the closure during its attachment to the syringe. In addition, any such improved closure, if developed, would preferably also be structured to provide a clear and unmistakable indication of tampering or of previous attempted access to the contents of the preloaded syringe. Finally, if any such improved closure and support for the closure were developed, it would also preferably be structurally and operatively reliable, while still remaining relatively easy and cost effective to make and use, in order to facilitate widespread use and acceptance throughout the medical profession. It would also be ideal if any such syringe closure were developed, for one or more components of the closure to include identifying codes, in a manner which facilitates the tracking thereof along a distribution route, which would allow for the history of a particular pre-filled syringe to be tracked, should that be desired or ever be needed.

SUMMARY OF THE INVENTION

The present invention is intended to present a solution to these and other needs which remain in the relevant field of art, and as such, is directed to a closure and a support for the closure, wherein the closure may include a tamper evident assembly, structured for being protectively connected to a syringe of the type including a nozzle and a discharge port. The present invention is further directed to a tracking system associated with the closure assembly comprising identifying codes disposed on components thereof, for tracking the closure assembly along a distribution route.

In at least one preferred embodiment, the present invention comprises a closure, and includes an end cap member and a syringe cap, the latter structured to define a rotational attachment to a syringe. When the closure is connected to the syringe, the syringe cap is disposed to restrict and/or prevent fluid flow from the discharge port of the syringe nozzle and further, is cooperatively structured with a tamper evident assembly within the end cap member to provide a clear indication of any near attempt to access or accomplished access to the contents of the preloaded syringe.

In addition, the end cap member includes an open end and a substantially oppositely disposed closed end, wherein the open end is dimensioned to receive the discharge port and/or nozzle of the syringe therethrough into the interior thereof. The closed end of the end cap member is fixedly secured, such as by sonic welding, to the end cap member, thereby serving to segregate the corresponding interior portion of the end cap member, at least adjacent to the closed end from an exterior of the end cap member. The syringe cap is disposed within the interior of the end cap member and is structured for rotational attachment to the syringe in a manner which serves to cover the nozzle in substantially flow restricting position relative to the discharge port of the syringe. Therefore, as should be apparent, the rotational attachment between the syringe cap of the end cap member and the syringe, in covering relation to a portion of the nozzle is accomplished by relative rotation between the syringe and the syringe cap.

Moreover, in certain instances, the syringe cap may be at least partially movable within the interior of the end cap member. Accordingly, a drive assembly is disposed on the interior of the end cap member and is structured to facilitate the rotational attachment of the syringe cap to the syringe. As described in greater detail hereinafter, the drive assembly is formed on interior portions of both the syringe cap and a correspondingly disposed interior portion of the closed end of the end cap member. Structuring of the drive assembly is such that the syringe cap will be prevented from rotating within the interior of the end cap member upon a confronting interaction between different portions of the drive assembly which, as set forth above, are located on interior portions of the syringe cap and the closed end portion of the end cap member. As a result of the interaction of the different portions of the drive assembly, the syringe can be at least partially inserted into the open end of the end cap member, such that rotation of the syringe relative to the syringe cap is facilitated by the syringe cap being disposed in a fixed orientation on the interior of the end cap member. A continued and sufficient rotation of the syringe relative to the syringe cap will accomplish the aforementioned rotational attachment therebetween and an effective mounting or securement of the closure to the syringe in covering and/or flow restricting relation to the nozzle and/or discharge port of the syringe.

Another operative and structural feature of one or more preferred embodiments in the present invention is the provision of a closure support including a support base. The support base may be structured to define a floor or another appropriate portion of the container may be structured to contain one or more of the closures on the interior thereof. In addition, the support base includes at least one connector or a plurality of such connectors equal in number to the number of closures intended to be maintained on the interior of the container or mounted on the support base. Each of the one or more connectors is disposed and structured to be removably connected to the closed end of a corresponding end cap member so as to maintain the end cap member in a substantially upright, operative orientation.

As will also be explained in greater detail hereinafter, the operative orientation of the one or more end cap members, when disposed on the support base, facilitates the aligned insertion of a portion of the nozzle of the syringe into the end cap member and the aforementioned rotation of the syringe relative to the syringe cap. As a result, the rotational attachment of the syringe and the syringe cap will be efficiently accomplished. Once attached, the syringe and the connected closure can both be removed from the support base and container, without any unnecessary handling of the closure.

More specifically, each of the one or more connectors is cooperatively structured with the closed end of each of the end cap members to define a "rotationally restrictive" connection between the end cap member and the support base. Such a rotationally restrictive connection there-between will be sufficient to prevent or at least substantially restrict rotation of the end cap member in either of two opposite directions, relative to the support base, while the nozzle of the syringe is being inserted into the interior of the end cap member and rotated relative to the syringe cap and end member. The aforementioned rotational attachment of the syringe and the syringe cap is further facilitated by a threaded engagement of the syringe and the syringe cap, along correspondingly and cooperatively structured portions thereof. Once the rotational attachment has been established, the corresponding, connected closure can be removed from the support base and/or from the interior of the container, defining the support base, by a lifting or other outwardly directed force being applied to syringe.

In addition, and in order to further help determine if attempted or actual tampering of the pre-filled syringe on which the closure assembly is connected might have occurred, the present invention also includes a tracking system in at least one preferred embodiment. More specifically, the tracking system comprises the identifying coding, such as through the application of a bar code, optically readable indicia, unique serial number or other forms of coded indicia to one or more components of the closure assembly, such as but not limited to, both the end cap and the syringe cap. As indicated, the coded indicia is not necessarily limited to a bar code but may assume other forms of code which may be electronically readable as well as visually observable. Further, the coded indicia applied to the various components of the closure assembly are structured to provide specific identifying information or data relating to the corresponding closure assembly. Moreover, coded indicia disposed on each of the closure assembly components may be identical or sufficiently similar to facilitate a determination that the various components are associated with the same closure assembly. In addition, the applied coded indicia will be structured to provide predetermined identifying information sufficient to determine the site and/or identity of the original manufacturer, as well as the distribution route from its manufacture site to its point of use. Moreover, the bar code or other coded indicia would include sufficient electronically readable data to facilitate the determination of production information such as, but not limited to, lot number, serial number, component identifying information, etc.

As also explained in greater detail hereinafter, the physical application of the coded indicia on the various components of the closure assembly may vary. Further by way of example, the bar code or other coded indicia may be imprinted on a label, which is subsequently attached to predetermined ones of the components of the same closure assembly. Also, the coded indicia could be "laser etched" on the components during and as a part of the manufacturing and/or assembling procedure of the closure assembly, prior to it being distributed and mounted on the pre-filled syringe.

Accordingly, one embodiment of the tracking system includes the disposition of the bar code or other form of coded indicia on an outer, observable portion of at least two of the components of the closure assembly. In a preferred application, the coded indicia would be imprinted both on an "interior component" such as the syringe cap as well as on an exterior, clearly observable component, such as the end cap. However, it is emphasized that the operative features of the tracking system are not limited to placing the coded indicia on these components. Furthermore, the individual indicia codes placed on different ones of the components of the same closure assembly would be sufficiently similar to provide clear recognition that the components, when scanned or otherwise observed, are part of the same closure assembly. This in turn will facilitate the tracking of the given closure assembly from its time of manufacture and assembly to the point where the end cap is separated from the syringe cap so as to obtain access to the prefilled syringe. Ideally, absent any unauthorized tampering or attempted access to the prefilled syringe, the various components of the closure assembly would remain connected to one another and in flow restricting relation to the prefilled syringe up until the time where the contents of the syringe is dispensed directly to the patient.

However, the existence of the tracking system of the present invention, in the form set forth herein, facilitates the efficient determination of the distribution route associated with the transport, delivery and use of the closure assembly as well as any of a possible plurality of intervening points along the aforementioned distribution route.

Moreover, the form of the coded indicia applied to predetermined ones of the multiple components of each of a plurality of closure assemblies should be capable of being "read" electronically by one or more commercially available or customized optical scanners or readers. In addition, the procedure used to apply the coded indicia to the selected closure assembly components should be such as to not interfere with or derogatorily affect efficient manufacturing and/or assembly techniques and procedures for the closure assembly.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 2:
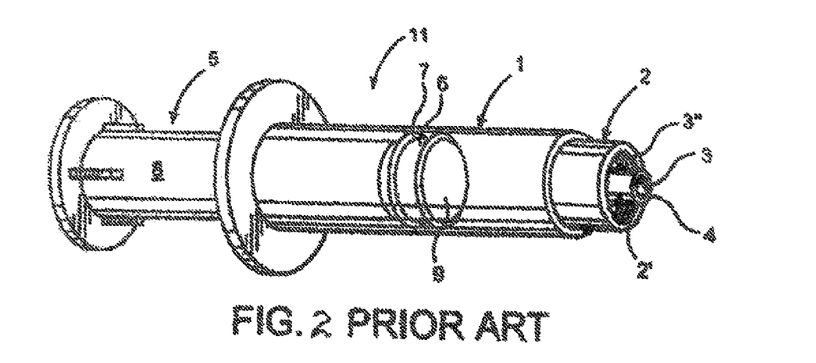
FIG. 2 is a prior art representation of a standard or conventional syringe.

As indicated in the accompanying drawings, the present invention is directed to a closure generally indicated as 20, which is structured for use in combination with a conventional syringe 11, of the type disclosed in the prior art representation of FIG. 2.

In describing the structural and operative features of the present invention, reference will be made to a conventional or standard type syringe 11 as shown in FIG. 2 labeled as "Prior Art." As such, the syringe 11 typically includes a barrel 1 and a nozzle structure 2. The barrel 1 comprises an elongate interior chamber disposed in fluid communication with an axial passageway or channel 3 on the interior of the nozzle portion 2'. Also, the nozzle portion 2' may comprise a luer type fitting. The channel 3 is to be considered a portion of the nozzle structure 2 and terminates distally at an opening or discharge port 4. A piston 5 is structured to slide within the barrel and includes a head 6 provided with a circumferential gasket 7. When assembled, the end face 9 of the head 6 of the piston 5 confronts the interior end of the channel 3 and closes the discharge port 4. The piston also includes a push rod or plunger 8 connected to the head 6, which is dimensioned to pass into the barrel 1. In use, the standard type syringe 11, after being loaded with its intended contents may be closed or sealed by covering the discharge port 4 with the closure 20 of the present invention. Accordingly, the nozzle structure 2 preferably includes an inner connecting surface 3" or other appropriate connecting structure, such as a ribbed or threaded surface. Therefore, and as has been represented, the interior connecting surface or portion 3" and the nozzle portion 2' can be and should be considered a part of the nozzle 2 for purposes of this description.

Figure 1:
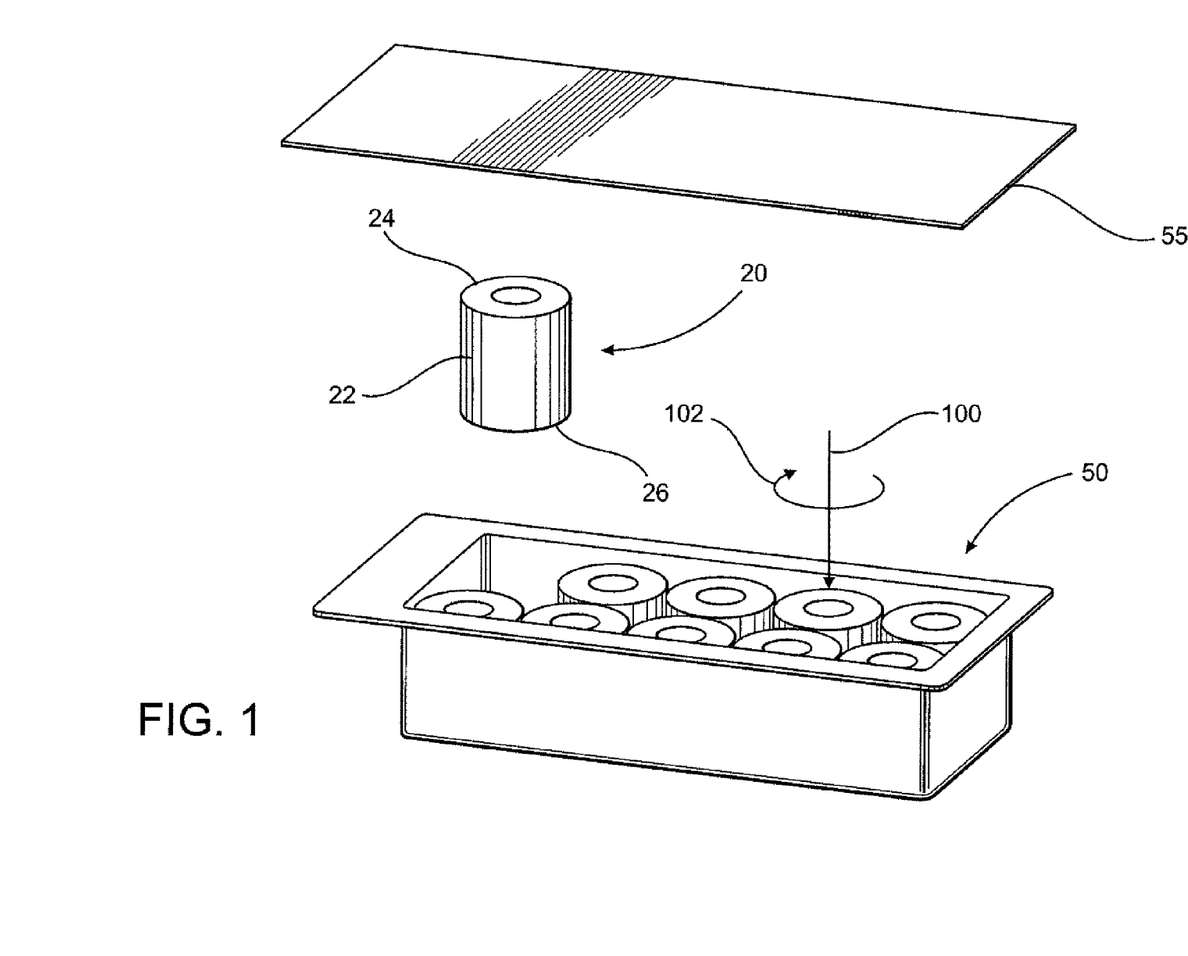
FIG. 1 is an exploded view of the closure and support for the closure representing at least one preferred embodiment of the present invention.
Figure 7:
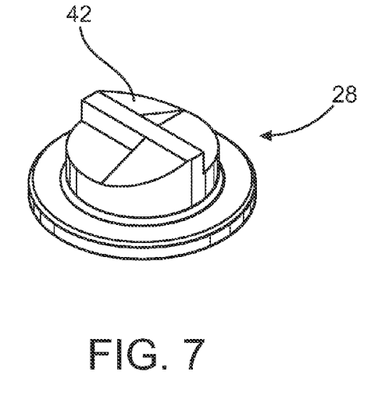
FIG. 7 is a perspective view in detail of a closed end of the closure of the embodiment of FIGS. 1 and 3.
Figure 8:
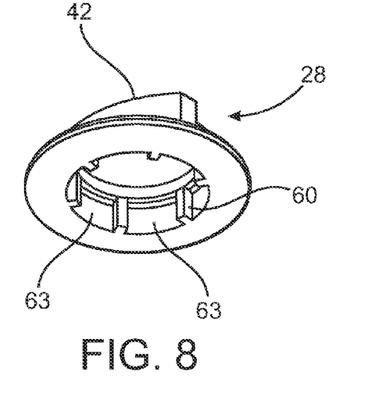
FIG. 8 is a bottom perspective view of the closed end of FIG. 7.

Referring now to FIG. 1, the structural and operative features of the closure 20 include an end cap member 22 having a substantially hollow interior that is at least partially defined by an open end 24 and an oppositely disposed closed end 26. With primary reference as well to at least FIGS. 3, 7 and 8, the end 26 of the end cap 22 is defined by a closed end portion 28 fixedly or integrally connected to the end cap member 22. The closed end 28 may be integrally formed with, or ideally, sonically welded to the end 26 so as to at least partially segregate interior portions of the end cap 22 at least in the area adjacent the end 26 from an exterior of the end cap member 22 and closed end 28. Additional structural and operative features of the closed end 28 will be described in detail hereinafter with regard to FIGS. 7 through 10.

Figure 3:
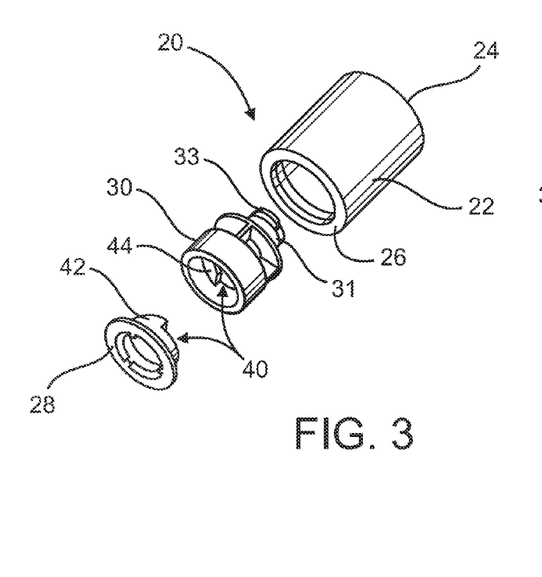
FIG. 3 is an exploded perspective view of the closure of the embodiment of FIG. 1.

As shown in FIG. 3, the closure 20 also includes the provision of a syringe cap 30 dimensioned and configured to be disposed within the interior of the end cap 22 in interactive relation with the closed end 28. Moreover, the syringe cap 30 is designed to be disposed in covering relation to the portion of the nozzle 2' so as to restrict fluid flow from the discharge port 4. The intended covering, flow restricting relation of the syringe cap 30 relative to the nozzle portion 2' is accomplished by the closure 20 and more specifically, the syringe cap 30 being rotationally attached to surface 3" of the nozzle 2 of the syringe 11.

Figure 5:
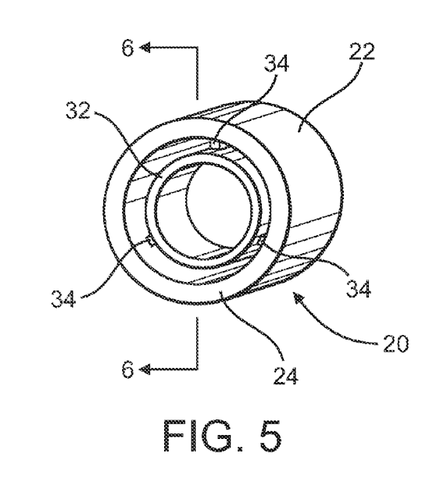
FIG. 5 is an interior perspective view of an end cap member of the embodiment of the closure as represented in FIGS. 1, 3 and 4 in association with a tamper evident assembly.
Figure 6:
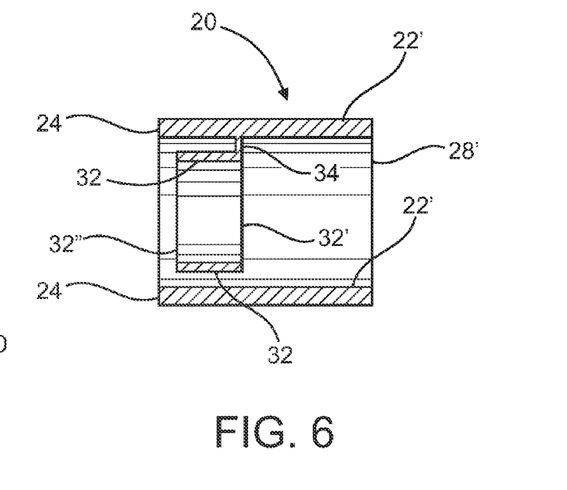
FIG. 6 is a transverse sectional view along line 6-6 of FIG. 5.

Additional features of at least one preferred embodiment of the closure 20 may include the provision of a tamper evident assembly, comprising an indicator member 32, as shown in FIGS. 5 and 6. The indicator member 32 preferably includes an annular or ring-shaped configuration, as shown in these Figures. In addition, the indicator member 32 is at least initially, but removably, connected to the interior surface portions 22' of the end cap member 22 by at least one, but more practically, a plurality of frangible members 34, as also shown in FIGS. 5 and 6. The opposite ends of the indicator member 32 are open, as at 32' and 32". Further, the inner, transverse dimension or diameter of the indicator member 32 is sufficient to receive at least a leading portion 31 of the syringe cap 30 therethrough, when the closure 20 is fully assembled.

Figure 4:
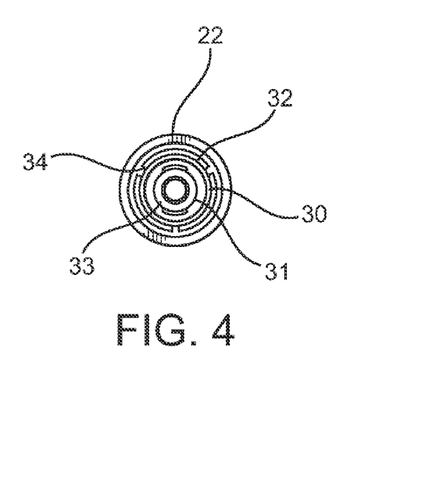
FIG. 4 is an end view of an open end of the embodiment of FIG. 3.

As shown in FIGS. 3 and 4, the closure 20 also includes the leading portion 31 of the syringe cap 30 which preferably, has outwardly extending tabs, ears and/or partial thread members 33. These tabs, ears or partial thread members 33 are disposed, configured and structured to interact with the threaded or ribbed interior surface 3" of the syringe's nozzle structure 2. Accordingly, when the various components of the end cap member 22 are assembled, the syringe cap 30 and in particular, the partial thread members 33 are disposable to interact with the threaded surface 3" to accomplish the intended rotational attachment between the closure 20 and the syringe 11. Such rotational attachment is accomplished by a relative rotation of the syringe 11 and the syringe cap 30, once the syringe cap member 30 is assembled on the interior of the end cap member 22. Such rotational attachment is further defined by a mating interaction of the partial thread members 33 and the threaded or ribbed surface 3", once a coaxial alignment and insertion is established between the nozzle portion 2' of the syringe 11 and the end cap member 22 and the syringe cap 30. Such an axial alignment and insertion is at least partially, schematically represented as 100 in FIG. 1 and is at least partially defined by the nozzle portion 2' protruding through the open end 24 of the end cap member 22, the open end 32" of the indicator member 32 and into the open end of the leading portion 31 of the syringe cap 30. When properly inserted, the threaded members or tabs 33 will be aligned with the threaded surface 3" of the syringe 11. When so aligned, the syringe 11 may be rotated relative to the end cap member 20 and syringe cap 30, as schematically represented at 102 in FIG. 1, to accomplish the required and intended rotational attachment between the syringe cap 30 and the syringe 11.

Referring now to FIG. 3, in order to further facilitate the aforementioned rotational attachment between the closure 20 and the nozzle structure 2 and/or nozzle portion 2', the closure 20 includes a one way drive assembly 40 comprising cooperatively structured drive portions 42 and 44. Each of the drive portions 42 and 44 include a "ramp and cliff" structure. Such a ramp and cliff structure of each of the drive members 42 and 44 provides for a fixed positioning of the syringe cap 30 on the interior of the end cap member 22, when the drive portions 42 and 44 are disposed in confronting relation with one another and when the end cap member 20 is rotated in one, predetermined direction. As a result, the attempted rotation of the end cap member 22 in a direction opposite to the one, predetermined direction will result in rotation of the end cap member 22 relative to the syringe cap 30.

Accordingly, and still referring to FIG. 3, the one way drive assembly 40, defined by the ramp and cliff structure of the drive members or portions 42 and 44 will mandate that the syringe cap 30 and the end cap member 22 will rotate in a common direction defined by the aforementioned one, predetermined direction. Therefore, rotational attachment between the syringe tabs and/or ears 33 and the interior threaded surface 3" of the syringe cap 30 and the nozzle structure 2, respectively, is accomplished by a rotation of the end cap member 22 in the aforementioned predetermined one direction relative to the syringe 11, thereby defining the aforementioned rotational attachment between the syringe cap 30 and nozzle structure 2 of the syringe 11.

Again with primary referenced to FIGS. 5 and 6, the tamper evident assembly including the indicator member 32 may be detached from the interior of the end cap member 22 by a pulling force being exerted on the end cap member 20 causing the frangible members 34 to rupture and be displaced from their interconnecting relation between the indicator member 32 and the interior surface 22' of the end cap member 22. As such, the removal of the end cap member 22, by virtue of a pulling force being exerted thereon, provides a clear indication that access has been attempted to the drug contained within the syringe 11, due to the fact that the syringe cap 30 will still remain in rotational attachment with the nozzle structure 2 and the indicator ring 32 will remain in surrounding relation to the syringe cap 30 and/or portions of the nozzle 2', after a forced removal of the end cap member 22.

As generally indicated above, the present invention is directed not only to the closure 20 but to a support for the closure, generally indicated as 50 as best illustrated in FIG. 1. As shown in FIGS. 1 and 11 through 14, however, the support 50 may be in the form of a support base 52 which may or may not be part of a container generally indicated as 54. As such, the support base 52 can be accurately described as a floor or base portion of the container 54 (shown in FIG. 12). As represented, the container 54 is structured to contain at least one, but possibly a plurality of the closures 20 on the interior thereof. Further, the container 54 may include a cover structure 55 (shown in FIG. 1) that is preferably, but not necessarily, formed of Tyvek® material produced by the E.I. DuPont Company, of Wilmington, Del. (or one or more of its subsidiaries). Moreover, the container 54 may be structured to retain one or more of the closures 20 in a substantially upright and operative orientation. When so oriented, the closures 20 may be stored, shipped and made readily available for attachment to a syringe 11, in the manner described hereinafter.

The advantages of the cover 55 or other portions of the container 54 formed of the aforementioned Tyvek® material is that such material is gas permeable but resistant to the passage of liquid or moisture therethrough. As such, a sterilant gas can pass through the cover of the container 54 and facilitate the one or more closures 20 being sterilized. The sterilized condition of the one or more of the closures 20 can also be substantially or at least partially maintained prior to and during their rotational attachment to a syringe 11 by eliminating or reducing the need to physically handle the closures 20 in order to accomplish the connection of the syringe 11 and the closure(s). As such, the attachment of the syringe 11 to or with any one of a plurality of closures 20 can be accomplished without a physical touching of the closures 20 by first disposing the nozzle portion 2' of the syringe in axial alignment with the leading portion 31 of the syringe cap 30, as schematically represented by directional arrow 100 in FIG. 1. Once so aligned, and further, when the interior threaded surface 3" of the syringe nozzle 2 is disposed in interacting, confronting relation with at least partially threaded members 33 of the leading portion 31 of the syringe cap 30, the aforementioned "rotational attachment" can be accomplished by a rotation of the syringe 11 in a predetermined direction, such as schematically represented by directional arrow 102, also shown in FIG. 1, relative to the end cap member 22 and the syringe cap 30.

Figure 11:
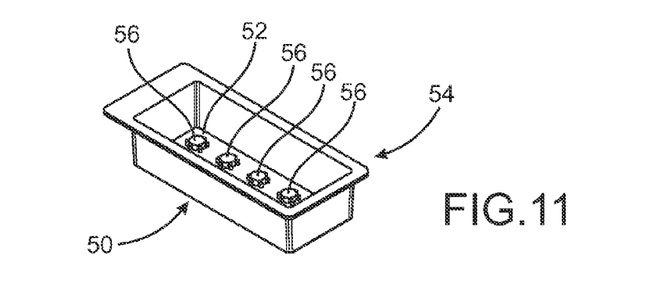
FIG. 11 is an interior, perspective view of the closure support of the embodiment of FIG. 1, wherein the support is in the form of a container.
Figure 12:
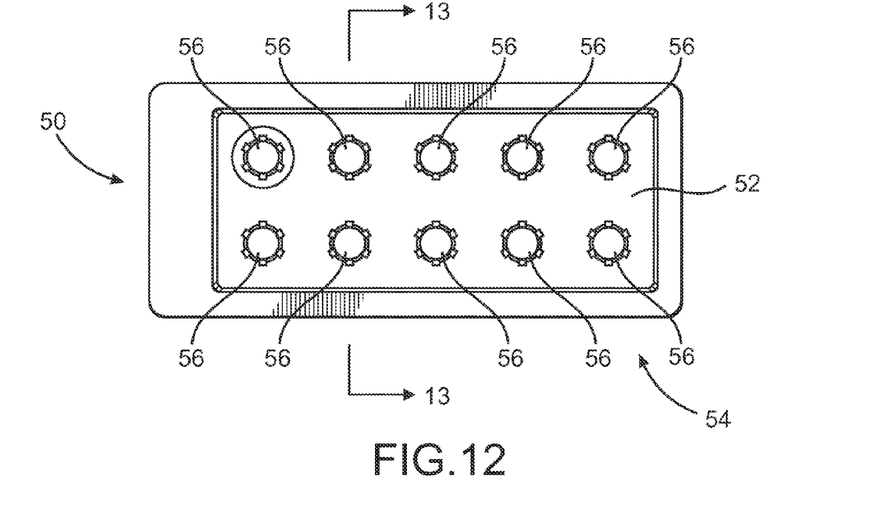
FIG. 12 is an interior, top plan view of the embodiment of FIG. 11.

Moreover, the aforementioned rotational attachment is further facilitated by maintaining each of the closures 20 in a fixed position while in the upstanding or upright operative orientation as demonstrated in FIG. 1. Due to the fact that the one or more closures 20 are fixed within the interior of the container 54 or in engaging relation with the support base 52, the syringe 11 will be able to rotate relative to the fixed position of the closure 20, thereby accomplishing the aforementioned rotational attachment between the nozzle 2 and the syringe cap 30. With reference now to FIGS. 11 and 12, and in order to facilitate the support and fixed operative orientation of the one or more closures 20 on the support base 52 and/or within the interior of the container 54, at least one or a plurality of connectors 56 are integrally connected to the support base 52 and/or floor portion of the container 54. Moreover, each of the one or more connectors 56 shown in FIGS. 11 through 13 are structured to interact with the exterior surface or portion of the closed end 28, specifically including an integrally formed recess or open ended chamber 60 formed on or within the exterior surface of the closed end 28.

Figure 9:
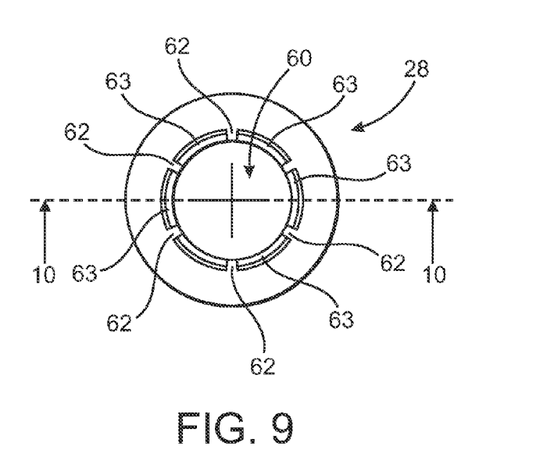
FIG. 9 is an exterior plan view of the closed end of the embodiment of FIGS. 7 and 8.
Figure 10:
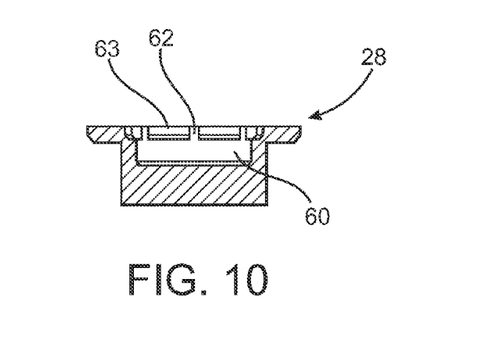
FIG. 10 is a sectional view along line 10-10 of FIG. 9.
Figure 13:
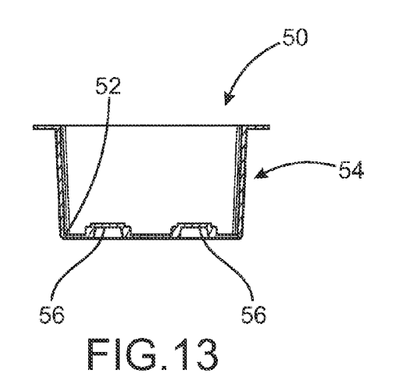
FIG. 13 is a transverse sectional view along line 13-13 of FIG. 12.
Figure 14:
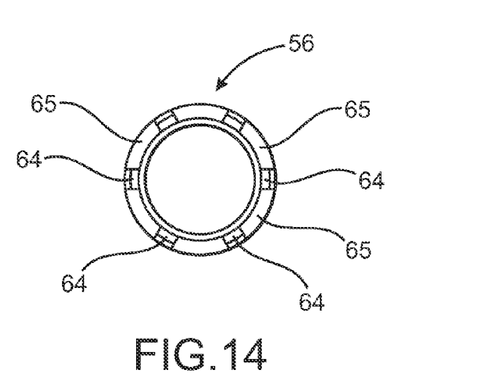
FIG. 14 is an exterior view of one of a possible plurality of connectors secured to and protruding outward from an interior of the floor of the container of the embodiment of FIGS. 1 and 11 through 13.

Still referring to FIGS. 11-13, the outwardly projecting one or more connectors 56 are cooperatively disposed, dimensioned and configured with the recess 60 formed on or within the exterior surface of the closed end 28 of the end cap member 20 to define a "rotationally restrictive" connection there-between. Such a cooperative structuring and interactive engagement or confronting relation between the connector 56 and a correspondingly disposed recess 60 (shown in FIGS. 8 through 10) will maintain an upright support of the corresponding closure 20. The "rotationally restrictive" connection may be more specifically defined with reference to FIGS. 9 and 10. As represented, the closed ends 28 of the end cap members 22 include a plurality of projections 62 formed at least partially on the interior side wall surface of the corresponding recess 60. The projections 62 may vary in number and placement but are cooperatively disposed, structured and dimensioned to interact with second plurality of projections 64 formed on an exterior surface of each of the connectors 56. Therefore, the cooperative dimension of the connectors 56 with the recesses 60 allow an at least partial insertion of the connectors 56 into the interior of a correspondingly disposed one of the recesses 60. When such insertion occurs the corresponding projections 62 of the closed end portion 28 and the additional projections 64 the connectors 56 will interact so as to be disposed in at least partially abutting or blocking relation to one another.

As a result, closed end 28 will be removably connected in a rotationally restrictive manner by being substantially prevented from rotating relative to the support base 52 in either of two opposite directions. The fixed attachment of the closed end 28 to the end cap member 22 will also rotationally restrict the end cap member 22 relative to the support base 52 in either of two opposite directions. Therefore, each of the closures 20, once disposed in the aforementioned rotationally restrictive connection with corresponding ones of the connectors 56 on the support base 52, will be prevented or at least restricted from rotating in either of two opposite directions. Such a restrictive rotation will substantially fix the position of the closure 20 relative to the support base 52 and facilitate the alignment 100 of the nozzle portion 2' with the interior of the syringe cap 30. This fixed positioning of the closures 20 in the upright, operative orientation will also facilitate the rotation of the syringe 11 relative to the end cap member 22 of the closure 20, as represented by the directional arrow 102. Accordingly, axial alignment 100 and the rotation of the syringe 11 in the preferred, predetermined direction 102 will result in an interactive engagement of the drive portions 42 and 44, thereby causing a fixed positioning of the syringe cap 30 relative to the end cap member 22 and support base 52. As a result, the aforementioned rotational attachment between the nozzle 2 of the syringe 11 and the syringe cap 30 will be made. Once such rotational attachment has been accomplished, an outwardly directed force or pulling force exerted on the syringe 11 will serve to remove the connected closure 20 from the interior of the container 54 and from its, operative orientation on the support base 52. The attachment between the end cap member 22 of the closure 20 and the syringe 11 may thereby be accomplished without the need for the individual to touch or handle the closure 20 and/or end cap 22.

However, the versatility of the closure 20 and closure support 50 of the present invention is further demonstrated by the ability to manually remove any one of the closures 20 from the support base 52 or from the interior of the container 54. Once so removed, the corresponding closure can be manually rotated relative to the syringe 11, and the aforementioned drive portions 42 and 44 of the drive assembly 40 will interact to facilitate the rotational attachment of the closure 20 and end cap member 22 to the syringe 11.

In addition to the above, the present invention is also directed to a tracking system for each of a plurality of closure assemblies 20. The tracking system is operative to facilitate the tracking of each such closure assemblies along a "path of distribution" from an initial point, such as their respective points of manufacture and/or assembly, to an end point, such as of authorized use. In more specific terms, the "path of distribution" or travel of each of the closure assemblies 20 may include applying a predetermined indicia code on at least two of the components of each closure assembly 20 during manufacture, assembly and/or packaging. As indicated, the coded indicia may be in the form of a bar code or other visually observable and/or electronically readable coded indicia disposed in an appropriate manner on the exterior of each of the at least two components of the same closure assembly 20.

Application of the specific coded indicia may be in the form of a label imprinted with a bar code, stamping, embossing and/or preferably by "laser etching" of the coded indicia on the selected components of the closure assembly 20. Further, the bar code or other coded indicia on each of the components of the same closure assembly 20 will be identical and/or sufficiently similar to efficiently identify each of the coded components as being associated with the same closure assembly 20. Moreover, the content of the coded indicia or bar code must include adequate information or data to efficiently track each of the closure assemblies from their point of manufacture or assembly to a point of authorized use. Such coded information or data may include a lot number, serial number, component ID number or letter, etc. The providing of each component with coded indicia which identifies it as being part of the same closure assembly should facilitate a determination of attempted or actual tampering. As set forth above, when tampering is attempted or accomplished in order to access the contents of a pre-filled syringe 11, the various components, such as the end cap 22 and the syringe cap 30, will be detached and separated. In such situations, a scanning or reading of the coded indicia of the separated components of the closure assembly 20, at various predetermined monitoring points along the distribution route, will facilitate a determination as to when and/or where such an unauthorized access to the prefilled syringe was accomplished or attempted.

In more specific terms, each closure assembly 20 will include the above-described end cap 22, which is removably connected to and encloses a syringe cap 30. As such, the selected bar code, optical scan or other coded indicia will be applied to an exterior or other readable location on each of these two components. Further, and by way of an example only, the coded indicia may be applied as follows: 1570(lot number)–1(serial number)–S or C("S" being representative of the exterior end cap sleeve 22; and "C" being representative of the interiorly located syringe cap 30). Therefore, when assembled, the closure assembly 20 will have both the end cap 22 and the syringe cap 30, with each having at least partially common, coded indicia applied thereto.

The tracking system of the present invention also provides for the "reading and/or recording" of the coded indicia of each of the closure assemblies 20 along the various points of its "distribution route" such as, but not limited to from its point of manufacture and/or assembly to its point of intended, authorized use of the prefilled syringe 11 on the patient. As such, the intended distribution route may include the registering, reading, etc. of the coded indicia of each closure assembly 20 once it is assembled at the point of manufacture. Thereafter, the distribution route may include a portion associated with the transport of the closure assemblies 20 from the point of manufacture to a location or area where they are attached to pre-filled syringes 11. At such a location, the coded indicia associated with each closure assembly could again be scanned or read, and subsequently registered indicating that the closure assembly was intact at the filling location. Thereafter, the combined closure assembly 20 and syringe 11 would be transported to a general location of use or distribution such as, but not limited to, a healthcare facility. The applied coded indicia could there again be read, scanned and registered, further indicating that at this point along the distribution route the closure assemblies were intact and mounted on the pre-filled syringe. Upon a more localized delivery of individual ones of the closure assemblies 20 and syringes 11 to a nursing station, or other dispensing station, the applied coded indicia could then be once again read and registered. This would again be evidence indicating that the syringe 11 and corresponding closure assembly 20 were properly delivered to at least a local point of distribution, further providing a determination that the closure assembly was intact and that the syringe had not been tampered with at this location along the distribution route. The distribution route may also include a scanning, reading or other recording of the applied coded indicia at the point of use, where the syringe is used to deliver medication to a patient. At this point, the end cap 22 would be removed from the syringe cap 30 allowing a reading and determination that the applied coded indicia of both of these components indicate that the closure assembly had remained intact and attached to the syringe immediately prior to use. Such an "end reading" would clearly indicate that no tampering had been attempted or accomplished of the contents of the prefilled syringe.

However, at any point along the above noted distribution route an attempted or accomplished tampering of the closure assembly 20 would result in a separation of the end cap 22 from the syringe cap 30. The reading of the coded indicia applied to the syringe cap, still remaining and/or at least partially separated from the syringe 11 would provide a clear indication of which particular closure assembly 20 had been tampered with. In turn, the precise distribution route which a given closure assembly 20 had followed from its point of manufacture to a location where tampering of the closure assembly 20 has become evident will be established. Appropriate investigation of the personnel associated with any given closure assembly 20 along the respective distribution route and/or the implementing of changes of security measures associated with a given distribution route could be more efficiently accomplished to prevent such tampering.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described.

What is claimed is:

1. A system for tracking a multiple component tamper evident closure assembly for a prefilled syringe along a distribution route, said tracking system comprising:
   a predetermined code comprising a plurality of coded indicia segments,
   said predetermined code structured to identify and distinguish each of a plurality of closure assemblies from one another,
   each of said plurality of coded indicia segments be at least electronically readable and applied to a different one of at least two assembled ones of the multiple components of a common one of the plurality of closure assemblies,
   each of said coded indicia segments being structured to identify corresponding ones of the multiple components as being associated with the same closure assembly,
   reading and recording observable portions of said predetermined code for each closure assembly along the distribution route of each closure assembly,
   defining the distribution route of each closure assembly as extending at least between a point of manufacture/assembly and a point of authorized use, and
   determining a location of tampering of a closure assembly along the corresponding distribution route by reading the coded indicia segments on either of detached ones of said two originally assembled components of the same closure assembly.

* * * * *